(12) United States Patent
Ha et al.

(10) Patent No.: US 11,715,560 B2
(45) Date of Patent: Aug. 1, 2023

(54) COMPUTER-BASED OPERATING ROOM SUPPORT SYSTEM

(71) Applicant: JOHNSON & JOHNSON SURGICAL VISION, INC., Irvine, CA (US)

(72) Inventors: Catherine P. Ha, Fountain Valley, CA (US); Timothy L. Hunter, Corona Del Mar, CA (US); Kenneth E. Kadziauskas, Coto de Caza, CA (US); Joseph E. Pedroza, Vista, CA (US); Mark E. Steen, Santa Ana, CA (US); Wayne S. Wong, Irvine, CA (US); Tamara Evans, Irvine, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 98 days.

(21) Appl. No.: 14/025,651

(22) Filed: Sep. 12, 2013

(65) Prior Publication Data

US 2015/0073816 A1    Mar. 12, 2015

(51) Int. Cl.
*G16H 40/63*    (2018.01)
*G16H 50/70*    (2018.01)
(Continued)

(52) U.S. Cl.
CPC ............ *G16H 40/63* (2018.01); *G16H 20/40* (2018.01); *G16H 50/70* (2018.01);
(Continued)

(58) Field of Classification Search
CPC ............ G06F 19/3481; G06F 19/3408; G06F 19/3443; G16H 50/70; G16H 40/63;
(Continued)

(56) References Cited

U.S. PATENT DOCUMENTS

| 5,444,842 A | 8/1995 | Bentson et al. |
| 6,125,350 A | 9/2000 | Dirbas |

(Continued)

FOREIGN PATENT DOCUMENTS

| EP | 1350367 B1 | 6/2006 |
| EP | 1305712 B1 | 9/2006 |

(Continued)

OTHER PUBLICATIONS

Klapan, Computer-assisted surgery and computer-assisted telesurgery in otorhinolaryngology, May 2006, Ear, Nose and Throat Journal, vol. 85, Issue 5, pp. 318-321. (Year: 2006).*

(Continued)

*Primary Examiner* — Christopher L Gilligan
(74) *Attorney, Agent, or Firm* — Johnson & Johnson Surgical Vision, Inc.

(57) ABSTRACT

A computer-based surgery support system and method for obtaining information of surgical procedures from networked equipment in an operating room, storing the retrieved information in a database, receiving a request for the stored information from a user terminal, and providing the stored information in accordance with the received request. The networked equipment may be configured for use in cataract surgical procedures, such as a phacoemulsification system.

45 Claims, 12 Drawing Sheets

(51) Int. Cl.
  *G16H 20/40* (2018.01)
  *G16H 40/20* (2018.01)
  *A61F 9/008* (2006.01)
  *A61F 9/007* (2006.01)
(52) U.S. Cl.
  CPC . *A61F 9/00745* (2013.01); *A61F 2009/00887* (2013.01); *A61F 2009/00891* (2013.01); *G16H 40/20* (2018.01)
(58) Field of Classification Search
  CPC .............. G16H 20/40; G16H 40/20; A61F 2009/00887; A61F 2009/00891; A61F 9/00745
  See application file for complete search history.

(56) References Cited

U.S. PATENT DOCUMENTS

| | | |
|---|---|---|
| 6,757,714 B1 | 6/2004 | Hansen |
| 7,046,134 B2 | 5/2006 | Hansen |
| 7,117,239 B1 | 10/2006 | Hansen |
| 7,149,792 B1 | 12/2006 | Hansen et al. |
| 7,185,014 B1 | 2/2007 | Hansen |
| 8,409,214 B2* | 4/2013 | Lonky ............... A61B 17/02 606/123 |
| 9,319,483 B2* | 4/2016 | Mussoff ............. H04L 67/01 |
| 2003/0055679 A1 | 3/2003 | Soll et al. |
| 2003/0159141 A1 | 8/2003 | Zacharias |
| 2003/0178489 A1* | 9/2003 | Boukhny ............. A61B 90/96 235/462.13 |
| 2004/0015079 A1 | 1/2004 | Berger et al. |
| 2005/0075578 A1 | 4/2005 | Gharib et al. |
| 2006/0015367 A1 | 1/2006 | Taylor et al. |
| 2006/0142740 A1* | 6/2006 | Sherman ............. A61B 1/0005 606/1 |
| 2006/0184407 A1 | 8/2006 | Ozaki et al. |
| 2006/0270913 A1* | 11/2006 | Todd ................... A61B 90/00 600/300 |
| 2008/0021711 A1 | 1/2008 | Claus et al. |
| 2008/0030345 A1* | 2/2008 | Austin ................ A61B 19/44 340/572.8 |
| 2008/0281301 A1* | 11/2008 | DeBoer ............... G06F 19/3487 606/1 |
| 2009/0190808 A1 | 7/2009 | Claus et al. |
| 2010/0001864 A1 | 1/2010 | O'Brien et al. |
| 2010/0076453 A1 | 3/2010 | Morris et al. |
| 2010/0287127 A1* | 11/2010 | Claus .................. G06F 19/3481 706/12 |
| 2011/0157480 A1* | 6/2011 | Curl .................... G16H 40/20 348/739 |
| 2011/0160583 A1 | 6/2011 | Roche et al. |
| 2011/0178821 A1* | 7/2011 | Smith .................. G06F 19/321 705/3 |
| 2011/0295887 A1 | 12/2011 | Palmese et al. |
| 2012/0046966 A1 | 2/2012 | Chang et al. |
| 2012/0302941 A1* | 11/2012 | Teodorescu ......... A61F 9/00745 715/863 |
| 2013/0123616 A1 | 5/2013 | Merritt et al. |
| 2013/0191154 A1 | 7/2013 | William et al. |
| 2014/0280474 A1* | 9/2014 | Lynn ................... G06F 19/3418 709/203 |
| 2015/0057675 A1* | 2/2015 | Akeel .................. G16H 40/63 606/130 |
| 2015/0073816 A1 | 3/2015 | Ha et al. |
| 2017/0061375 A1 | 3/2017 | Laster et al. |

FOREIGN PATENT DOCUMENTS

| | | | |
|---|---|---|---|
| WO | WO-2004058049 A2 * | 7/2004 | ............. A61B 34/70 |
| WO | 2008031010 A2 | 3/2008 | |
| WO | 2010074781 A2 | 7/2010 | |
| WO | WO-2010129916 A2 | 11/2010 | |
| WO | WO-2012093330 A1 * | 7/2012 | ......... H04N 5/23225 |
| WO | 2015054290 A1 | 4/2015 | |

OTHER PUBLICATIONS

Ritsma, Reining In The New Equipment, Oct. 2004, Surgical Products, vol. 23, Issue 10, pp. 14-15. (Year: 2004).*
Partial International Search Report for Application No. PCT/US2014/055436, dated Dec. 15, 2014, 7 pages.
International Search Report and Written Opinion for Application No. PCT/US2016/049992, dated Nov. 29, 2016, 11 pages.
International Search Report and Written Opinion for Application No. PCT/US2014/055436, dated Jul. 10, 2015, 17 pages.
Koeny M., et al., "A New Telesupervision System Integrated in an Intelligent Networked Operating Room," The Third International Conference on Emerging Network Intelligence, 2011, pp. 39-44.
Yashar A.G., "Better Phaco Technology Yields Better Outcomes," Ophthalmology Times, Jul. 1999, vol. 24 (14), 3 pages.

* cited by examiner

COMPUTER-BASED OPERATING ROOM SUPPORT SYSTEM

CROSS-REFERENCE TO RELATED APPLICATIONS

N/A

TECHNICAL FIELD OF THE INVENTION

The present invention is generally related to methods, devices, and systems related to apparatuses used in all types of eye surgery, such as for controlling surgical fluid flows and the like. In particular, the disclosed methods, devices, and systems may be used to improve practices in surgeries such as cataract, Lasik, laser cataract, vitreoretinal, glaucoma, etc.

BACKGROUND

A cataract is a clouding of the natural lens of the eye which leads to a decrease in vision, eventually resulting in blindness. The visual loss occurs because the clouded lens obstructs light that would otherwise pass through the lens to the retina at the back of the eye. Cataracts are commonly treated with a surgical procedure to remove the clouded natural lens from the eye and replace it with a clear artificial lens. Phacoemulsification refers to a stage of cataract surgery in which the eye's natural lens is emulsified by applying ultrasonic energy to the lens with a handpiece, and aspirated from the eye by applying a vacuum tube to the emulsified lens material. During the procedure, irrigation is performed and aspirated material is replaced using a balanced salt solution, thereby maintaining pressure in the interior of the eye. The emulsified and aspirated lens is replaced with a clear artificial intraocular lens (IOL).

To perform such a procedure, a surgeon often utilizes a computer-controlled system of specialized equipment called a phacoemulsification system to ultrasonically emulsify and aspirate the natural lens of the eye prior to inserting the IOL. Phacoemulsification systems use various computer programs for performing various tasks, controlled in part by adjusting settings of the programs to drive motors and pumps, for example, to emulsify and aspirate the subject lens material and to do other tasks necessary to complete the surgery. Different phacoemulsification systems may provide different programs. Further, different programs may be used in different situations. The program settings selected typically take into account the particular subject eye on which surgery is performed based for example on measurements of the eye and various other aspects of the patient's physiology.

The duration of a cataract surgical procedure commonly varies from about five to about forty minutes or more. Information pertaining to the procedure is generally monitored and recorded by equipment in the operating room or by operating room staff during the procedure. The equipment in the operating room may include a microphone and/or video camera, the phacoemulsification system, and the like. Information monitored and recorded before, during, and after the procedure may include information such as the time needed to set up and prepare the operating room, the length of the procedure, the amount of ultrasonic energy applied to the lens to emulsify it, medications and other supplies consumed during the procedure, characteristics of the IOL implanted, the time needed to clean the operating room after the procedure, patient recovery time, and the like. During the procedure, information such as the amount of energy applied to emulsify the lens, the amount of vacuum applied to aspirate, the flow rate, a microscopic view of the operating field, and the like, may be displayed on a user interface of the phacoemulsification system, or on a separate screen, computer, or other viewing device, and may be monitored and verbally reported by support staff during the procedure. At least some of this data, along with doctor's notes of the procedure, is commonly placed manually in the patient's file after the conclusion of the procedure.

If data such as the emulsifying energy applied to the lens is not recorded during the procedure, retrieving such data from the surgical equipment is inconvenient, and may be difficult to accomplish. Moreover, phacoemulsification system data from previously performed cataract surgeries is not conveniently organized.

Further, if a surgeon requests a summary of a plurality of such procedures, for example, an informational summary of surgeries performed during a particular day in the past, or a summary of surgical case data and energy usage over a period of time, the staff must perform a painstaking, time-consuming, manual process of retrieving patient files, accumulating the desired data, and formatting it for presentation. In some prior art systems, electronic data collection methods are available but are limited to downloading information of surgical procedures from the phacoemulsification system onto a USB stick and copying it to a computer for decoding, compiling, formatting, and reporting.

One way to determine the length of a procedure is to record a video of the surgical procedure and thereafter review the video of the procedure, noting the time at the beginning and end of the procedure. The surgical procedure may be recorded by a so-called Surgical Media Center (SMC), which creates a video of the procedure and may record other surgical data during the surgery in real time. An SMC will typically record certain predetermined data, but cannot keep track of everything. Moreover, although the SMC can record the procedure on video, it cannot determine on its own when the actual procedure began or when the procedure is deemed complete.

Further, SMC and phacoemulsification system program settings, such as which aspects of the procedure are recorded, are a matter of personal preference of the surgeon, and thus can vary from one surgeon to another leading to inconsistent results. Typically, the surgeon selects apparatus settings appropriate for a particular procedure, but may not remember all of the settings actually in use during each procedure. If a question subsequently arises regarding what the actual settings used were during a particular procedure, the surgeon may defer to his SMC/phaco equipment specialist to determine the settings that were used, or may wait until the next available opportunity to visually review the settings of the relevant apparatus and then manually write them down for future reference. If the surgeon wishes to modify SMC and/or phaco system settings from one procedure to another, or copy a set of settings from one unit to another, she/he must manually change the system settings or export the settings to a recording medium such as a USB stick to be copied onto the other machine. These processes are inconvenient and prone to error.

In addition, a large variety of supplies are consumed during a typical cataract surgery. Tracking and replacing the consumables is a manual process that typically involves a purchaser manually interacting online with a supplier ordering system, or directly contacting a customer service department of a supplier to place an order.

SUMMARY

A computer-based surgery support system, including an application executable on a mobile device and arranged to interface with one or more operating room device or system that is coupled to a data communication network. The operating room may be arranged to perform or support any type of surgery including eye surgeries, such as cataract, Lasik, laser cataract, vitreoretinal, glaucoma, etc., surgeries. In embodiments, the operating room equipment may include one or more of a computer-based phacoemulsification system, a Surgical Media Center (SMC), and a laser machine. The application can provide access to surgical procedure data, including the start and stop times and duration of a procedure, energy applied to a lens during phacoemulsification, and settings of the phacoemulsification system programs. Responsive to a user request, the application may automatically present a predetermined selection of information in a predefined format, and record select information of each procedure in respective patients' electronic files or in a summary report for easy cross-referencing with a patient's file. The support system also provides for convenient centralized storage of respective surgeons' preferred surgical media center and/or phacoemulsification system program settings, tracks the operation of phacoemulsification system programs during a procedure, and allows changes to those settings between procedures. The support system also tracks consumables used during procedures, and provides an interface to order entry systems to place orders and replenish inventory. System users may also share data and information with other users and systems.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate disclosed embodiments and/or aspects and, together with the description, serve to explain the principles of the invention, the scope of which is determined by the claims.

In the drawings.

DETAILED DESCRIPTION

Figure 1:
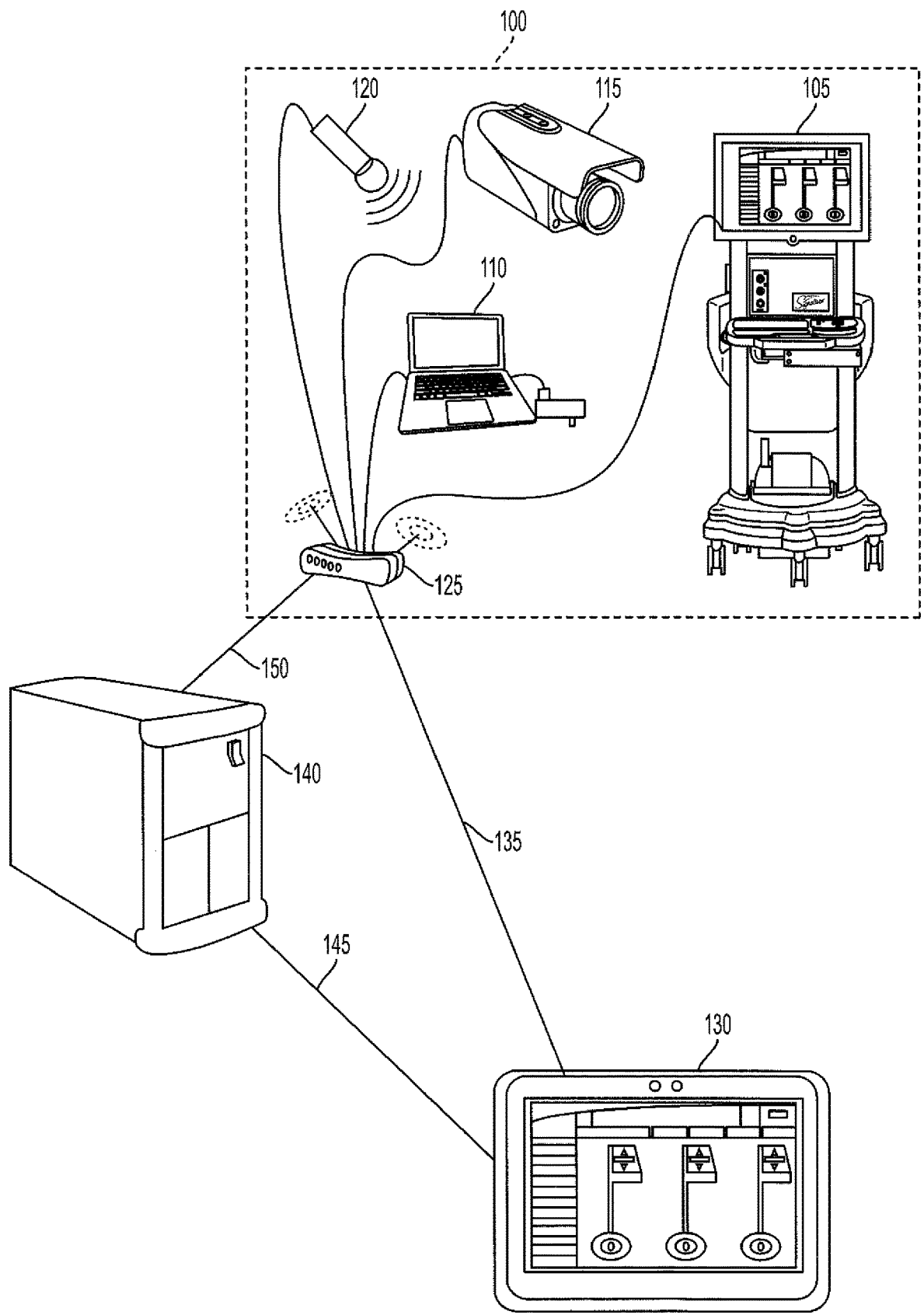
FIG. 1 illustrates a diagram of an exemplary computer-based cataract operating room system according to the disclosure.

It is to be understood that the figures and descriptions provided herein may have been simplified to illustrate aspects that are relevant for a clear understanding of the herein described apparatus, systems, and methods, while eliminating for the purpose of clarity other aspects that may be found in typical apparatus, systems, and methods. Those of ordinary skill in the pertinent arts may recognize that other or additional elements and/or steps may be desirable and/or necessary to implement the apparatus, systems, and methods described herein. Because such elements and steps are well known to those of ordinary skill, and because they do not facilitate a better understanding of the herein disclosed apparatus, systems, and methods, a discussion of such elements and steps may not be provided herein. However, the present disclosure is deemed to inherently include all such elements, variations, and modifications to the described aspects that would be known to those of ordinary skill in the pertinent arts.

The herein disclosed apparatus, systems, and methods provide to a user with a networked user terminal the ability to interact with one or more devices or systems having a network interface in an operating room. The operating room may be arranged to perform or support eye surgeries, such as, for example, cataract, Lasik, laser cataract, vitreoretinal, glaucoma surgeries. In embodiments, the operating room equipment may include one or more of a computer-based phacoemulsification system, a Surgical Media Center (SMC), a laser machine, and the like. With the user terminal, the user may obtain information from the operating room equipment, either directly via their respective network interfaces, or indirectly through a server that obtains information from the operating room equipment. The network interfaces of the operating room equipment and the user terminal may be wired, such as interfaces to Ethernet networks compliant with IEEE 802 network interface standards, or may be wireless, such as air interfaces to cellular data, Bluetooth, or WIFI networks. The user terminal may be a mobile device such as a smart phone, tablet, portable computer, personal desktop computer or the like. The communication network may be private or public, and may include communication over the Internet.

The system thus communicatively couples the user terminal to the operating room equipment, either directly or through an intermediary server, enabling retrieval of select information of one or more surgical procedures, and allowing the retrieved information to be presented to the user in a predetermined format, which may include tabular, graphical, and/or textual information. The user may also obtain operating room equipment settings, surgical case data, energy usage (e.g. phaco energy), and the like. Such equipment settings may be stored for later use in another cataract operation procedure. Further, the settings may be modified by the user for use in another procedure.

In embodiments, an application running on the user terminal or on the server may analyze the retrieved information, for example, to determine operating room trends, generate metrics such as the average time between cases, apply select filters, and set thresholds. The analyzed information may then be formatted for such uses as presentations. For example, the application can determine and format for presentation a listing a limited number of procedures by efficiency, for example.

Thereby, the system can facilitate surgical procedure efficiency improvement in several ways. For example, an intra-case timing profile may be developed that provides an estimate of how much time is remaining during various stages of a multi-stage procedure. The estimate may be modified based on a particular surgeon's preferences to reflect that surgeon's probable timing profile. The profile may include any identified activities involved in a surgical procedure, such as pre-surgery activities, patient preparation, surgical instrument preparation, and the like. Operating room management and notifications may thereby be based on an analysis of past doctor performance. For example, the analysis may include an analysis of only an identified doctor's past procedures, and/or may include an analysis of past performances of a plurality of doctors. The analysis may thus provide an estimate during a multi-stage surgical procedure of how long before the current stage is completed, or how long before the next stage begins, how long the rest of the entire procedure is likely to take, for example. The estimate may be modified in real time to account for tasks that arise during a procedure that deviate from the norm, such as performing a vitrectomy that lengthens the surgical procedure, for example.

In embodiments, the obtained operating room data may be reviewed on the user terminal using one or more applications and/or application modules running on the user terminal. In addition, information of a plurality of procedures may be obtained, compiled, analyzed, formatted, and provided to the user terminal responsive to a user request. The data may be analyzed in any desire manner, for example, to determine if the surgical process or operating room is functioning efficiently. Thus, in embodiments a user may use a user terminal to view information of procedures the user participated in, or may view, information of other users' data. In embodiments, the user may select which surgical procedure stages, features, or other elements are included in a requested analysis. Thereby, the user may determine how efficient others are compared to the user's own performance, for example.

The use of surgical equipment used during a procedure may be obtained, and one or more metrics developed to characterize various aspects of the procedure. Such procedure aspects which may be stored include a phacoemulsification system hand piece tip size, pump type used, lens density, or patient-specific complications encountered such as Intraoperative Floppy Iris Syndrome (IFIS), and the like.

In an embodiment of the present invention, such information may be used to generate a procedure evaluation score that provides an efficiency indicator. Such an indicator may take into account any aspects of a cataract operation procedure or plurality of procedures that are deemed relevant by a user. For example, an indicator can be developed using the system to account for a particular combination of elements and information such as lens density, hand piece type, energy applied, for example. The developed score may be stored for the use of the particular user alone, or may be shared as desired. For example, a score may be stored in a user file and used as a basis for comparing a plurality of procedures. Further, accumulated data from one or more machines may be used to create scores designed by a user to provide comparative indicators based on facility, and/or geographic operating region, for example.

Applications running on or accessible via a user terminal may provide a user with the ability to retrieve networked operating room equipment program settings, such as program settings of a phacoemulsification system. The settings may be saved at the user terminal or at the server. In addition, settings maybe modified for future use. Further, a plurality of groups of settings may be developed by a surgeon, for example based on a plurality of procedures performed on a range of different patients, in different facilities, using various equipment with various staff and/or having other situationally relevant aspects. Groups of settings may be developed for use by the surgeon in different anticipated environments. A select group of settings may be retrieved and used to set up networked operating room equipment before a procedure, based on the peculiarities of the particular operating environment. In an embodiment, a select group of settings may be applied to multiple operating room equipment or systems via the network and user terminal.

In an embodiment, a user terminal may be used to obtain historical data stored on the user terminal, phaco system, server, and/or SMC, to analyze trends of selected cases as an aid to determine modified settings on phaco systems and the like. In an embodiment, a user terminal may be used to obtain stored historical data to analyze trends of select cases. In embodiments, an application on the user terminal or phaco system may use such analyses to make suggestions regarding modifications to user settings on the phaco or other systems improve technique, outcomes, and/or efficiency. In addition, historical data may be used to suggest other available technology that may be used with the phaco system, or upgrades that may be downloaded to the system, such as to adjust, optimize, and/or improve the user's techniques, outcomes, and/or efficiency.

In an embodiment of the present invention, a user terminal may be used to obtain information of procedures performed. An application running on the user terminal or on a server can be arranged to organize the obtained data so that it is meaningful to the user, such as in a chart, table, text, or the like. This data, and other information such as videos from a networked surgical media center (SMC) located in an operating room may be accumulated and analyzed over time. Such data may be used for many things, including retrospective studies.

In an embodiment of the present invention, a "start procedure" button may be provided on a device or system in the operating room, for example on the phaco machine, to indicate when a procedure is beginning and ending, and/or when each stage of a staged procedure is beginning/ending. This may provide a consistent, reliable basis on which to determine the timing and efficiency of procedures performed in the operating room. If the button is in coupled to an SMC in the operating room, it may be used to invoke the recording functions of the SMC. Thereby, procedures performed by different surgeons may be put on a more consistent base, rendering time-based comparisons more valid. In the prior art for example, some sites may define the beginning of a procedure as when a "Prime" button or the like is pressed, while others may define the start of a procedure as when the surgeon presses a foot pedal. In an illustrative operation, the "start procedure" button may be pressed twice at the beginning of a procedure. The first press may initiate the SMC recording, and the second press may signify the formal beginning of the procedure. Similarly, the completion of a procedure can be signaled either by a user act such as pressing an "end procedure" button, or by performing an act that ordinarily indicates the end of a procedure, such as ejecting a tubing pack from a phacoemulsification machine.

In an embodiment of the present invention, operating room data may include a video recording of a view of the operational field under a microscope during the procedure, in addition to other real time surgical procedure information from the phaco system or the like. Further, the video signal of the microscope view, and/or an audio or video signal of the operating room from the SMC, may be streamed to the network. Thereby, an application running on the user terminal may serve as an independent monitor. For example, a surgeon or nurse in a break room can see what stage the procedure is at in a nearby operating room. In another example, students at a teaching institution can view a live surgery from a lecture hall, or on their personal devices while the procedure is being performed at a surgery center. In an embodiment of the present invention, a user terminal application may support multiple views simultaneously on the same screen, such as multiple view of the same room, or views of a plurality of operating rooms. Moreover, a plurality of user terminals may be used to monitor the same audio or video feed.

In an embodiment of the present invention, voice confirmation or voice control may be used with the system. For example, voice commands may be used to activate the SMC and identify activities of the procedure to the SMC for recording. In embodiments, a networked microphone may be used to take verbal notes, which may be overlaid on an SMC recording in real time during the procedure, or later during a review of the SMC recording, such as for use in creating notes for the surgical procedure. Such audio notes may be included in the patient file for reference.

In an embodiment of the present invention, a networked server in data communication with the networked operating room equipment may be used to obtain and store information of surgical procedures. Applications that operate on the obtained data may then be executed either at the server, or at user terminals, or both, such as distributed applications that have executable elements on both the server and the user terminal. In addition, the server may be arranged to provide a portal for users to access and share their data with other users and may act as an ecommerce server for executing transactions involving the obtained data.

The server may be arranged to interface with one or more supplier purchasing systems to enable users to more easily purchase items pertaining to the operating room. For example, with regard to a phaco system, the server may be used to obtain software updates of applications already installed on the phaco system, or new features not yet installed, such as language packs, for example. The server may be used to order accessories and supplies used in the operating room, such as surgical equipment, packs, tips, sleeves, intraocular lenses, and the like. In an embodiment of the present invention, the server can be arranged to automatically order supplies that have been consumed, for example, after each procedure, or periodically in accordance with a set schedule, or as triggered by inventory levels dropping to a predetermined threshold.

In an embodiment of the present invention, the server may be arranged to provide direct or indirect access to a supplier customer service center, and may be used to create customer service requests. Further, the server may be arranged to interface with one or more user email systems/accounts, and may be used to email SMC recorded videos to interested parties such as patients or associates. The server may also be arranged to provide an online forum, such as a social network, where users can create threads and discuss items of interest with each other.

In an embodiment of the present invention, the server may be arranged to obtain customer feedback. For example, online forms may be provided to patients to solicit their feedback regarding the effectiveness of their procedure, both in the short term and longer term over defined intervals of time. For example, an email may be sent to patients every six months inviting them to access the server online to participate in a survey and to provide comments and updates regarding their ongoing condition. Moreover, information may be obtained from online forums hosted on the server or accessible to the server, such as, for example, a social network.

In an embodiment of the present invention, the server may be used to host software demos, training videos, equipment manuals, new product information, advertising, and the like, which may also be accessed via a user terminal. In addition, tools for surgeons and other operating room personnel may be hosted and provided online via the server. For example, lens calculators such as the toric calculator, lens alignment tools, and other diagnostic tools may be made available and/or provided in an updated and real time manner to the user. The tools may be available on the user terminal, the phaco system, SMC, other operating room equipment, and/or server, and information from the tools may be transferred there between.

Supplies used may also be tracked with a reading device, such as, for example, a networked bar code reader, in data communication with the server, by reading barcodes of supplies consumed during the procedure. The user terminal can be used to view information stored on the server such as usage charts showing the supplies that were used. Supplies may be replenished automatically by the system, or may be re-ordered manually using information provided by the system. The reading device may take the form of a smartphone having an application for facilitating the reading of a barcode, for example, or other type of identifying tag, such as a NCF tag, or the like.

In an illustrative operation, a surgeon who has just purchased a modular ophthalmic microsurgical system, such as phacoemulsification system, may also acquire a separate user terminal at the same time for interacting with the system. The surgeon may use the app to browse settings used by himself or by other surgeons, and may retrieve preferred settings or edit retrieved settings as desired. Preferred settings may then be uploaded to a select phaco system for use during a procedure.

In another illustrative operation, after completing a days' worth of surgery, a head nurse may use a user terminal to obtain, accumulate, analyze, format, and review the day's procedures, and store them in a file.

In embodiments, formatted information may include one or more of operating room efficiency, energy usage flow rate, vacuum rate, procedure time, time between procedures, procedures per selected time period, characteristics of a plurality of surgeons, characteristics of a plurality of operating room staff persons, and a comparison of supplies used in a plurality of procedures. Further, the analysis results may include a correlation of information pertaining to a plurality of surgical procedures, efficiency, product usage, and phacoemulsification system program settings.

In yet another illustrative operation, the surgeon may view video demos hosted on the server regarding phaco system software features already obtained or available for purchase. The surgeon may purchase a desired feature and install it on a select phaco system. The surgeon may also obtain and install operational settings with regard to the purchased feature for the type of procedures the surgeon performs using the phaco system. Illustratively, the surgeon may install new features on a trial basis at no or reduced cost. Further, the surgeon may post comments to a forum hosted on the server regarding the trial features. As more surgeries are performed the server may be arranged to automatically accumulate relevant procedure data, for example, to develop common procedure timing profiles.

In a further illustrative operation, the surgeon may use the voice over function to overlay audio onto the SMC files, and save the edited SMC files for later use, such as for a podium presentation.

As noted, the server may be arranged to host and/or monitor relevant user forums, and may discover customer feedback through the forum that identifies desired product enhancements, which may lead to the development of product improvements.

Referring now to FIG. 1, a cataract operating room support system is illustrated. Network attached equipment in an operating room 100 in which cataract surgery is performed may include a computer-based phacoemulsification system 105, computer-based surgery media center (SMC)

110, as well as other equipment such as video camera 115 and microphone 120. Other devices (not shown) may also include a microscope and/or additional viewing screens. Each networked device has a network identifier, such as an internet protocol IP address, which may be used to access the device over the network. The equipment may be coupled to router 125, which may perform a network address translation (NAT) function to the operating room equipment coupled thereto, as is known in the art. Computer-readable information may be obtained from the operating room equipment from user terminal 130, either directly via network connection 135, or indirectly via server 140 via network connections 145, 150.

Figure 2:
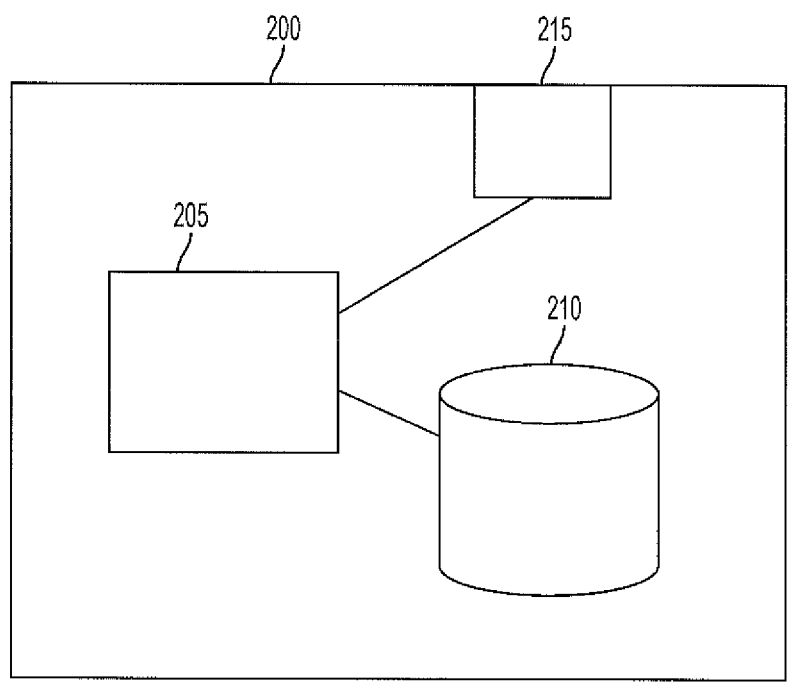
FIG. 2 illustrates a computerized device in accordance with the disclosure.

FIG. 2 is illustrative of a computerized device 200 representative of aspects of user terminal 130, server 140, SMC 110 and phaco system 105. Computerized device 200 is capable of executing software, such as an operating system (OS) and a variety of computing applications. The operation of exemplary computerized device 200 is controlled by computer readable instructions stored in a computer readable storage medium 210, such as a hard disk drive (HDD), optical disk such as a CD or DVD, random access memory (RAM), solid state drive, a USB "thumb drive," or the like. Such instructions may be executed within central processing unit (CPU) 205 to cause computerized device 200 to perform operations. Typically, the CPU is implemented in an integrated circuit called a microprocessor. In operation, the CPU fetches, decodes, and executes instructions from storage device 210. Such instructions may be included in software such as an operating system (OS), executable programs such as the herein described applications, and the like.

The user terminal, SMC, and phaco system may also comprise a display for viewing visual output generated by computerized device 200, responsive to operation of the aforementioned computing program, such as an app. Such visual output may include text, graphics, animated graphics, and/or video, for example. The display may be implemented with an LCD or LED-based or other flat panel display, for example.

Network adapter 215 may provide access to a network which may include one or more of a local area network (LAN), wide area network (WAN), Internet, an intranet, an extranet, or the like. The network provides remote access to computerized device 200 for transferring software and information electronically. Additionally, the network may provide for distributed processing, which may involve more than one cooperating computerized devices in performing a task. It is appreciated that the network configurations described are exemplary and other means of establishing communication links between computerized device 200 and remote users may be used. Network interface 215 may communicate with the network using any available wired or wireless technologies. Such technologies may include, by way of non-limiting example, wired and wireless interfaces such as gigabit ethernet, wifi, cellular data, or the like.

It is appreciated that exemplary computerized device 200 is merely illustrative of a computing environment in which the herein described systems and methods may operate, and does not limit the implementation of the herein described systems and methods in computing environments having differing components and configurations. That is to say, the inventive concepts described herein may be implemented in these or other computing environments using these or other components and configurations.

Computerized device 200 may be deployed in networked computing environment such as that illustrated in FIG. 1. In general, the above description for computing system 100 applies to server, user terminal, and computerized operating room equipment coupled to a networked environment, in which the herein described apparatus and methods may be employed. Network communications may use one or more known communication protocols, such as hypertext transfer protocol (HTTP), file transfer protocol (FTP), simple object access protocol (SOAP), wireless application protocol (WAP), or the like. Additionally, the networked computing environment may utilize various data security protocols such as secured socket layer (SSL), pretty good privacy (PGP), virtual private network (VPN) security, or the like. Each network attached device may be provided with an operating system able to support one or more computing and/or communication applications such as a web browser, email, user interfaces, medical device controls, and data analysis and formatting applications and the like discussed herein.

Embodiments of the herein disclosed apparatus, systems, and methods may include one or more applications (apps) running on a user terminal or networked server in a computing environment such as that discussed above with respect to FIGS. 1 and 2. The app may interface directly with computer-based devices in the operating room in substantially real time, or may interact with a device through a server. In particular, the phaco system may employ user-selected application program control settings to control aspects such as vacuum rate, flow rate, aspiration rate, ultrasound power applied using a hand piece, bottle height, pressurized infusion rate, cut rate, diathermy power, and the like.

One or more of the phaco system(s), the server(s), or user terminal(s) may accumulate, or "log", data of a single surgical or a plurality of procedures, and store the data. Such data may include information from procedures, settings programmed by a doctor or scrub nurse, etc. Stored data may be shared or transferred between the phaco system(s), the server(s), the SMC(s), and/or user terminal(s). Such sharing or transferring may occur automatically based in a program running on one or more of the phaco system, the server, SMC, and/or the user terminal. Similarly, the sharing and/or transfer of data may occur responsive to a user request or instructions input using the user terminal.

Logged information may include phaco device settings and parameters, phaco application and/or sensor operation, surgical device parameters and actions taken using a surgical device, and the like. Information pertaining to the surgeon, the patient, the equipment and the like may also be monitored and stored. The logged data may thus be saved, uploaded, or downloaded, such as for repeated use by a surgeon in different operating rooms, or in connection with certain patient parameters.

Such tracking and logging capability may further allow, for example, for inventory tracking across one or many facilities. For example each facility, or a plurality of co-owned or controlled facilities, may have secure access to the server which, through the aforementioned data logging, provides information regarding supplies used during one or more procedures. Thereby, each facility may automatically replenish inventories of supplies, for example, when inventory drops below a threshold.

In an embodiment of the present invention, the disclosed apparatus, systems, and methods may be used to remotely interact with Abbott Medical Optics Inc.'s WHITESTAR Signature® phacoemulsification system other similar types of systems. A universal app may be provided, for example, for execution on a user terminal such as an iPhone®, iPad®, or tablet that allows for remote interaction with the phaco system. The app may allow for navigation of the controls of the phaco system by displaying on the user terminal a screen similar to that displayed on the screen of the phaco system in the operating room.

Figure 3:
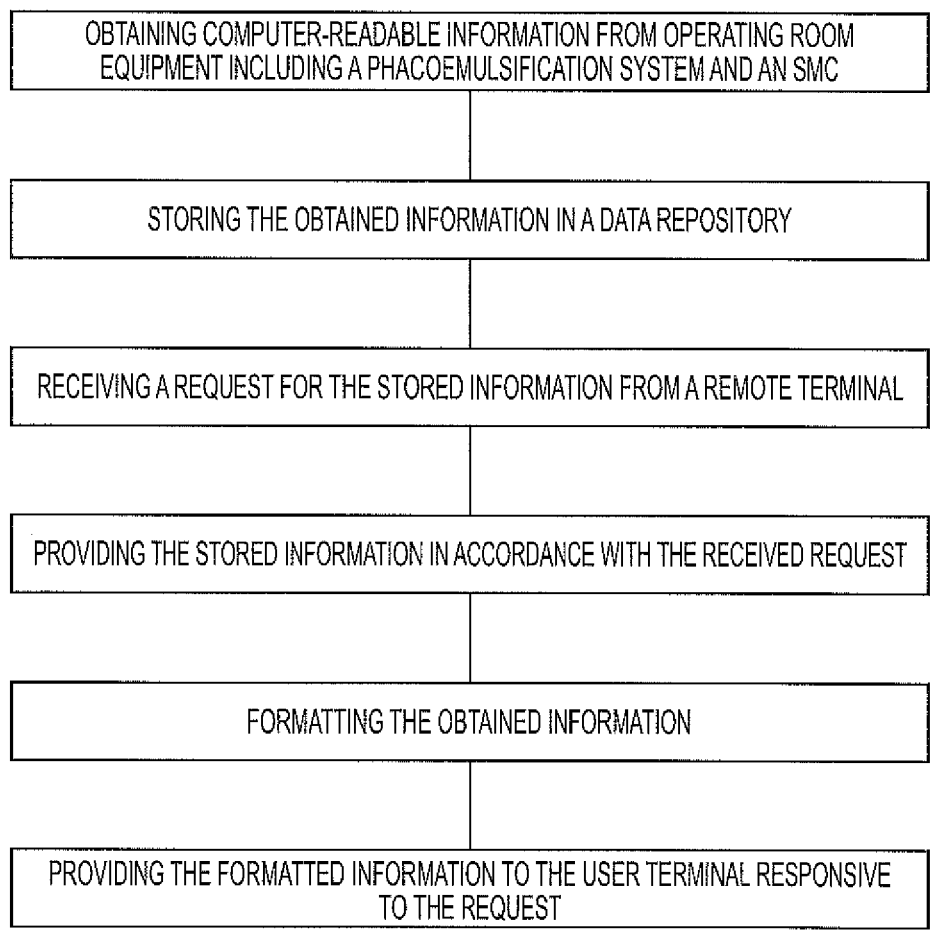
FIG. 3 illustrates a method of using a computer-based cataract operating room system according to the disclosure.

In accordance with embodiments described herein, and with reference to FIG. 3, there is shown a cataract surgery support method comprising obtaining computer-readable information from a network attached computer-based phacoemulsification system running at least one application utilizing selected settings during a cataract operation procedure in a cataract operating room, and storing the obtained information. The information may be stored at the user terminal used to request the information, or may be stored in a remote server. Thereafter, a user may request the stored information from the user terminal. In addition, computer-readable information may be obtained from a surgical media center (SMC), for example, an audio recording and/or a video recording of activity in the operating room during the cataract operation procedure. Surgeon-dictated audio may be overlaid onto the SMC data.

Thus, the obtained information includes at least one of diagnostic information, selectable settings, and operational information recorded during the procedure, of the phacoemulsification system used during the procedure. If the surgical procedure includes a plurality of stages, the obtained information may include information of each stage, such as the date and time of the beginning and end of each of the stages of the procedure, and of the beginning and end of the entire procedure.

Further, the obtained information may include identifiers of persons present during the procedure, including a patient on whom the procedure is performed, a surgeon performing the procedure, and operating room staff participating in the procedure and an indicator of their respective duties. The obtained information may also include information of supplies consumed during the procedure, including the identity of the supplies and the respective amount used. An application running in the system, for example on the server or in a user terminal, may automatically place an order for operating room supplies to replenish those consumed during the procedure.

The user terminal may be used to request information of one or more operating room procedures. For example, a user may select one or more data items for analysis and display the output in a predefined format. An application running on the user terminal or on a server may format the obtained information, and may provide the formatted information to the user terminal responsive to the request. Information of a plurality of cataract operation procedures may be compiled and analyzed. For example, an application may be configured to perform a predetermined analysis and format the results in a predetermined manner. The user terminal may then be used to request an updated analysis. Responsive to the request, the results of the analysis may be provided to the user terminal. The results may be formatted for display on a particular user terminal using identifying information of that terminal, for example. For example, the formatted information may include one or more of operating room efficiency, energy usage (e.g. effective phaco time (EPT)), energy usage over time, flow rate, flow rate over time, vacuum rate, vacuum rate over time, procedure time, time between procedures, procedures per selected time period, characteristics of a plurality of surgeons (e.g. number of surgeries per period of selected time, settings used, etc.), characteristics of a plurality of operating room staff persons (e.g. operating room turnover rate, etc.), error logs for use by service technicians (e.g. system errors) and/or operating room staff and doctors (user errors, such as errors indicating the foot pedal is not attached or a disposable component is not attached properly attached to the system), and a comparison of supplies used in a plurality of procedures. Illustratively, the analysis results may include a correlation of information pertaining to the plurality of surgical procedures, efficiency, product usage, and phacoemulsification system program settings.

The request may include a type identifier of the user terminal, and the formatting provided may be selected for presentation on the identified user terminal type. For example, the remote terminal may be one of a smart phone, a tablet computer, a portable computer, and a desktop computer, and the requested information may be formatted for presentation on the particular user terminal. The presentation format may be chosen from predefined templates or created and/or customized by the user.

Preferably, the operating room support system includes security mechanisms to protect access to data pertaining to procedures. In embodiments, user access to the system, such as access by a user terminal, includes user authorization. Thereby, non-authorized users are denied access to data. Further, different authorization levels may be included, such as to restrict a user's ability to modify data, or to modify settings, etc. Such authorization may include at least password or other knowledge-based protection, but may also include other security mechanisms such as biometric identifiers, encryption using hard or soft encryption keys, and the like.

In embodiments, diagnostic information such as log files may be retrieved from one or more systems. Such information may be obtained, for example, by a technician, on a routine basis during regular maintenance, or responsive to a customer call, question, or complaint. The log files would contain error information to assist with diagnosing/troubleshooting problems.

In an exemplary embodiment, a smartphone user terminal may run an app that will retrieve information directly from a phaco system such as Abbott Medical Optics Inc.'s WHITESTAR Signature® phacoemulsification system via a wireless network connection. The smartphone may retrieve surgical information pertaining to effective phaco time (EPT), and surgical time (ST) per case, summarize information by surgeon, and develop chart information for graphical representation of data. That may include one or more of the number of cases by surgeon and/or surgeon program, average EPT usage, and totals by surgeon. The app may also retrieve data for a select specific predefined period of time, e.g., 7, 30, 90 days, or a user-defined time period. Obtained information may include the total time for a procedure (start to finish), operating room turnaround time, a graphical representation of a day's surgical procedures, etc.

Illustratively, the smartphone application may retrieve data directly from the WHITESTAR Signature® System, or may retrieves data via a network facility, such as the Abbottlink network. The system may indicate EPT usage per case, and reduces the need to record values following each case.

Figure 4:
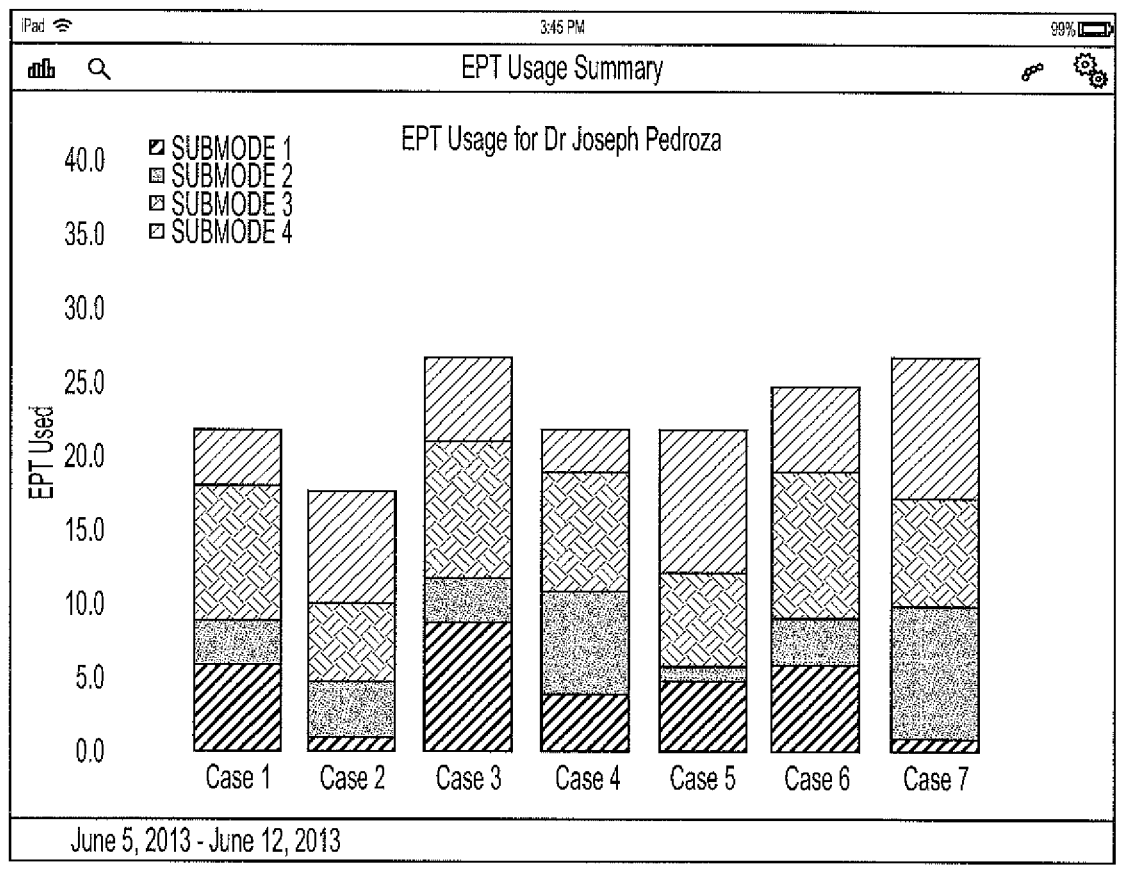
FIGS. 4-12 show exemplary charts and graphs illustrating the display of information provided by the system on a user terminal.

FIGS. 4-12 show exemplary charts and graphs illustrating the display of information provided by the system on a user terminal. FIG. 4 shows an illustrative stacked bar chart that shows EPT times by case. The bars separate energy used in each of a plurality of submodes. The EPT usage may be selectable by date.

Figure 5:
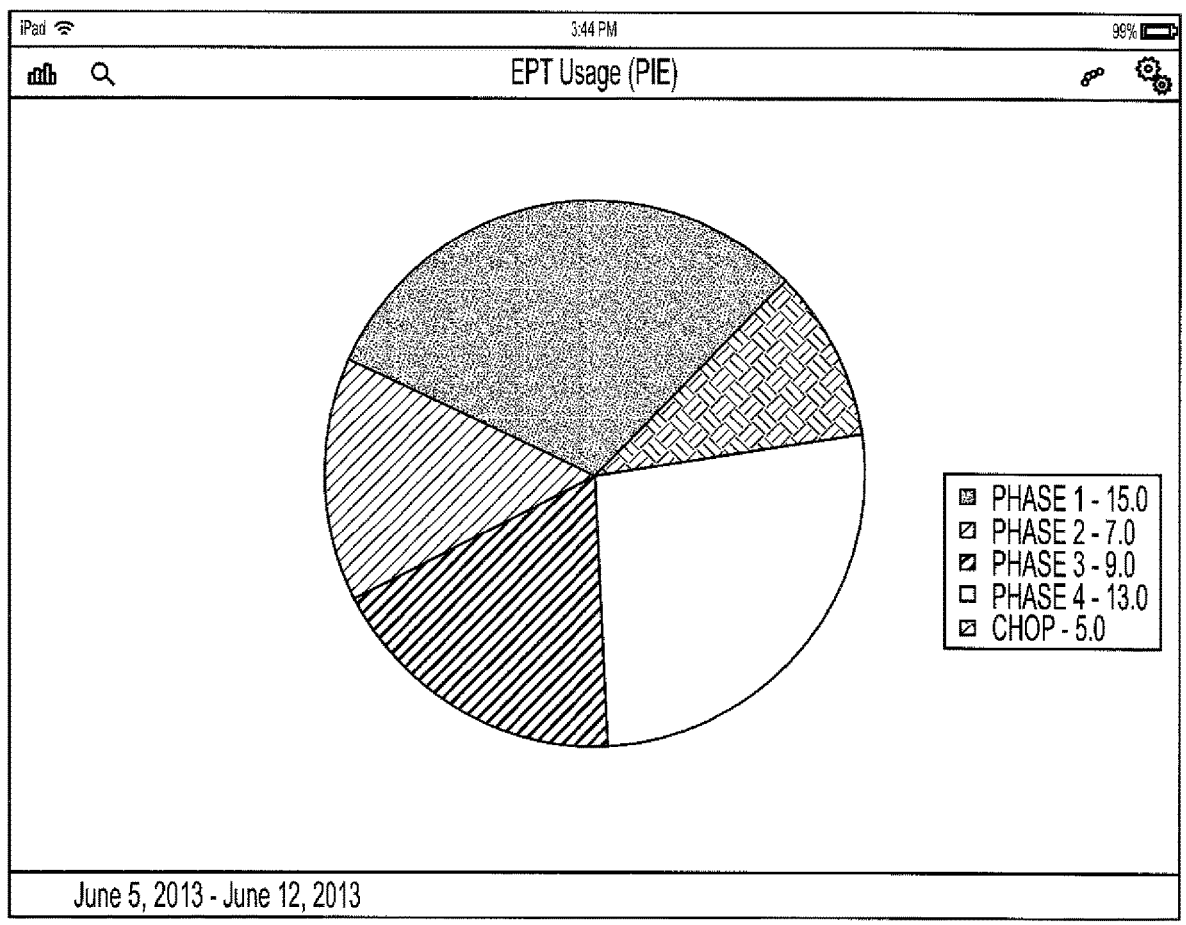

FIG. 5 shows an illustrative pie chart summarizing average EPT times by surgeon. As shown, surgeon EPT usage is averaged over a period of time. The chart shows a breakdown of use and accumulated EPT by submode.

Figure 6:
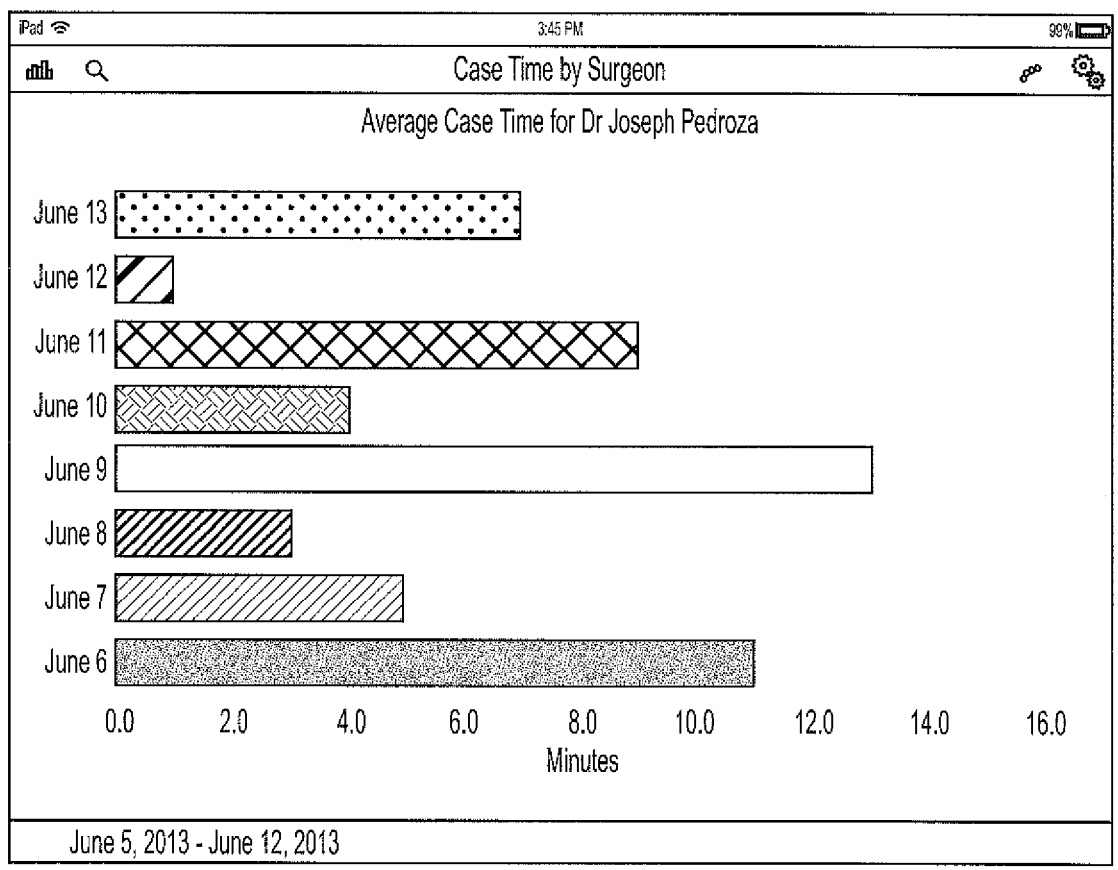

FIG. 6 shows an illustrative bar chart summarizing average case time by surgeon. The chart summarizes surgical procedure time for a surgeon over a given period. Averages are based on the actual number of cases in the day. The time period may be selectable or customizable.

Figure 7:
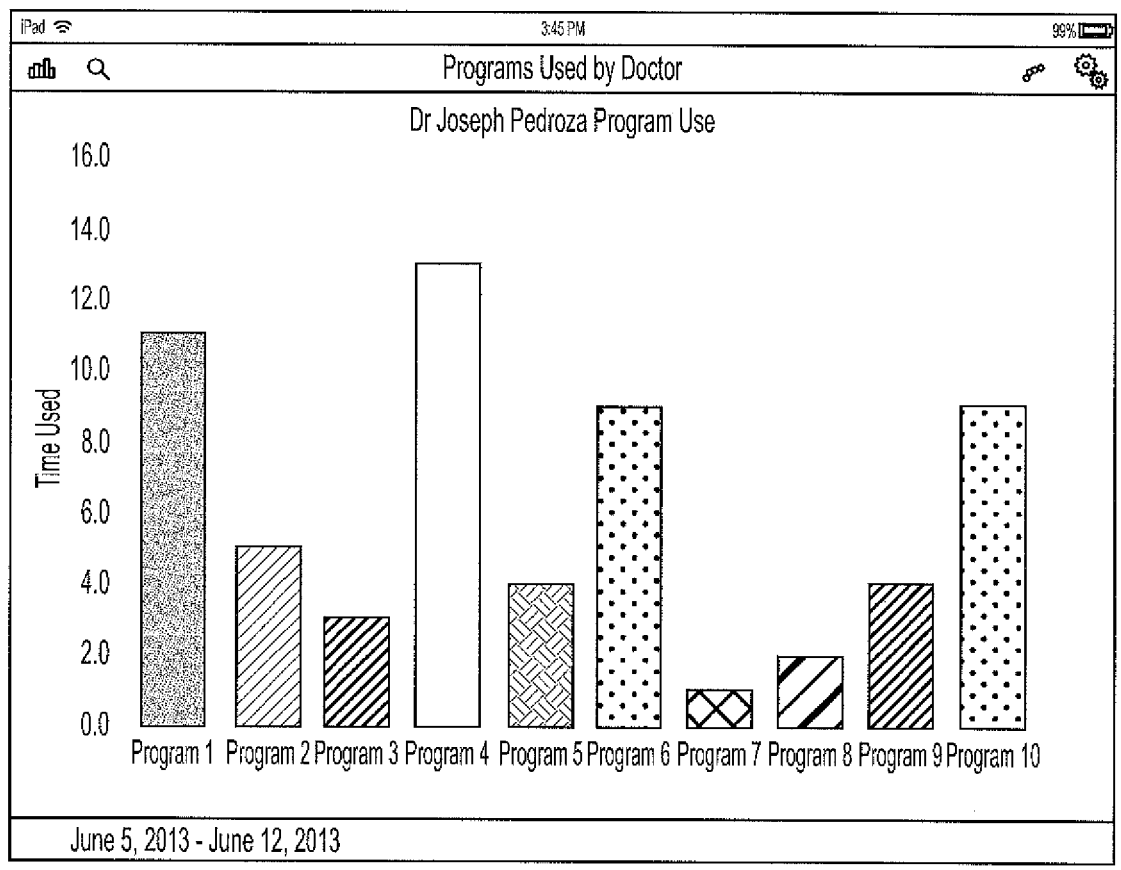

FIG. 7 shows an illustrative bar chart showing total cases for a surgeon by program. The chart shows surgeon program usage, and identifies how often a particular program was used over a given time period (shown at the bottom of the screen).

Figure 8:
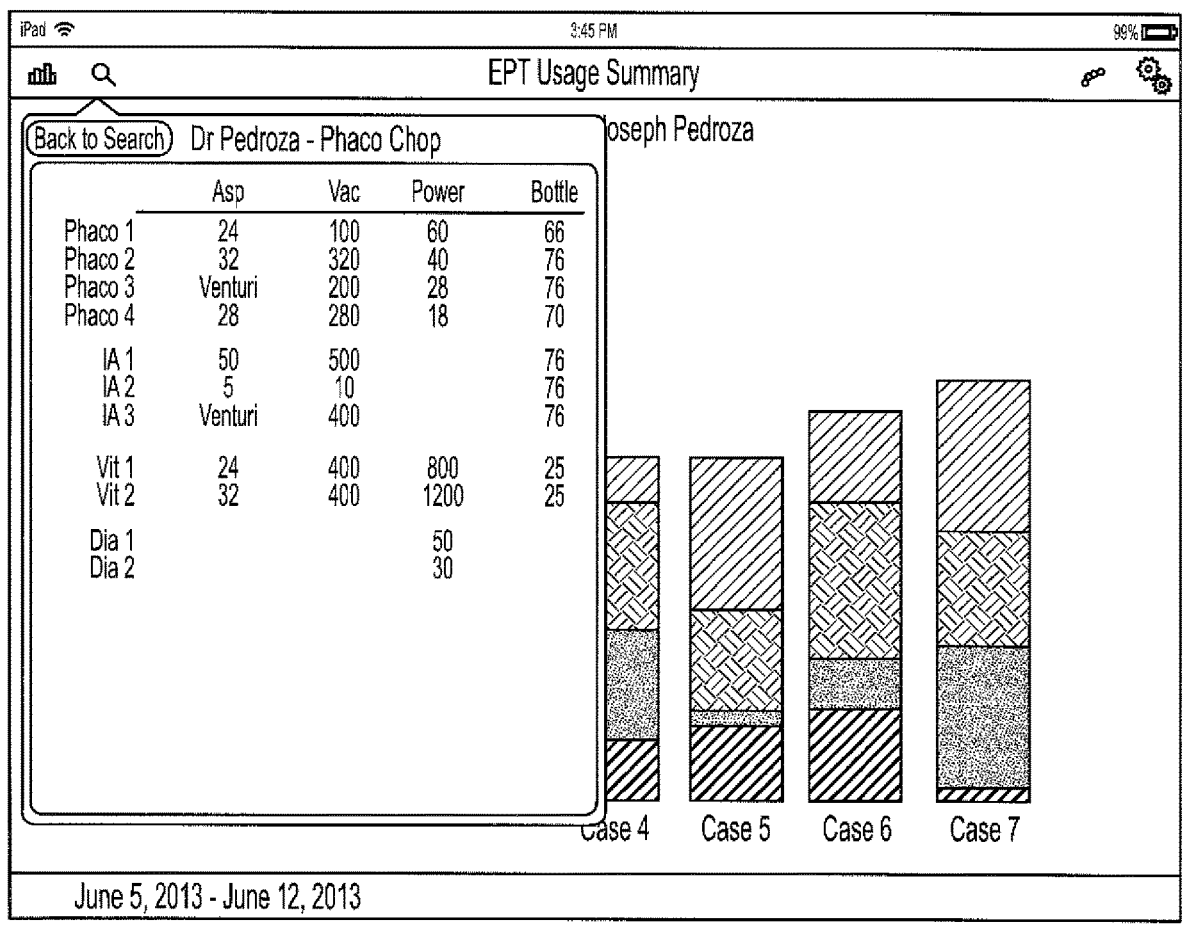

FIG. 8 shows an illustration of surgeon information and doctor programs. The chart shows a snapshot of surgeon program settings shown as a drop down window. It identifies main surgical parameters, which may be selectable by surgeon and program.

Figure 9:
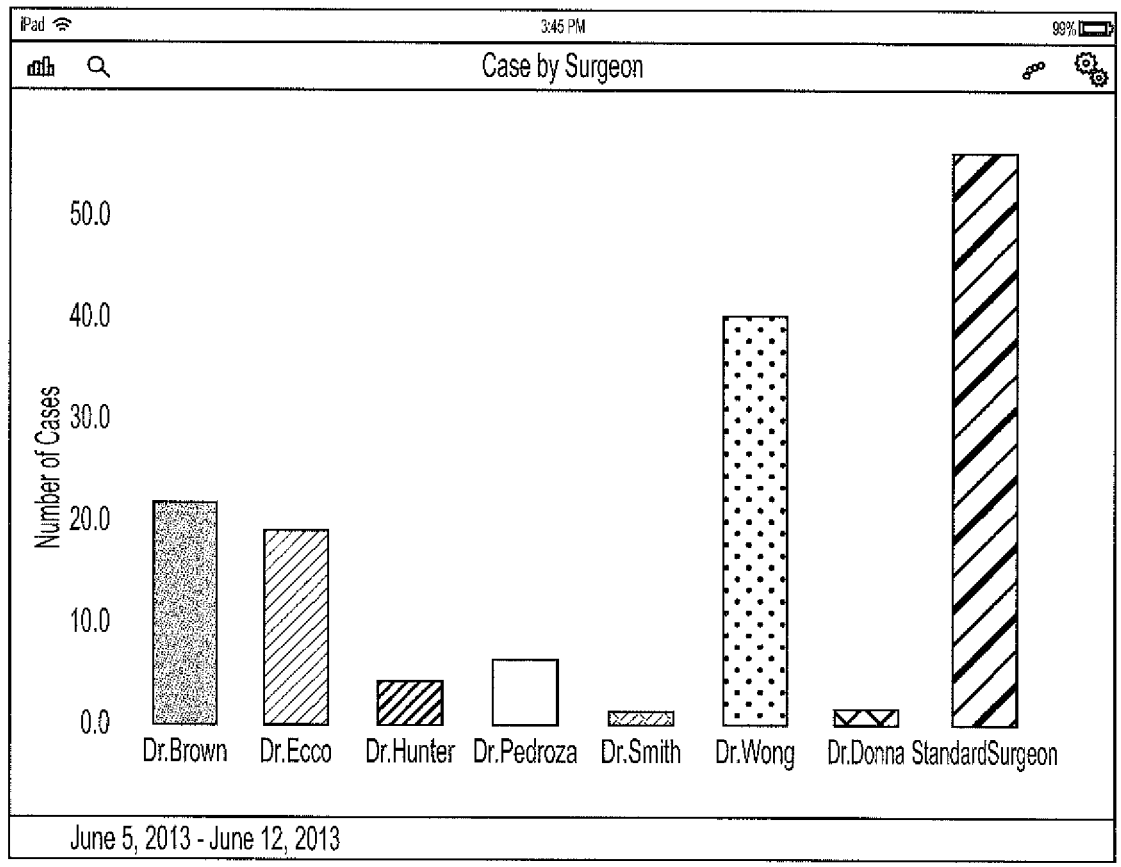

FIG. 9 shows a bar chart comparing numbers of cases by surgeon. The chart identifies how many cases were performed, and by which surgeons. It can help a user to understand who is using the system. It is also useful in identifying disposable inventory usage, and can be used to launch an inventory replenishment app and/or interface.

Figure 10:
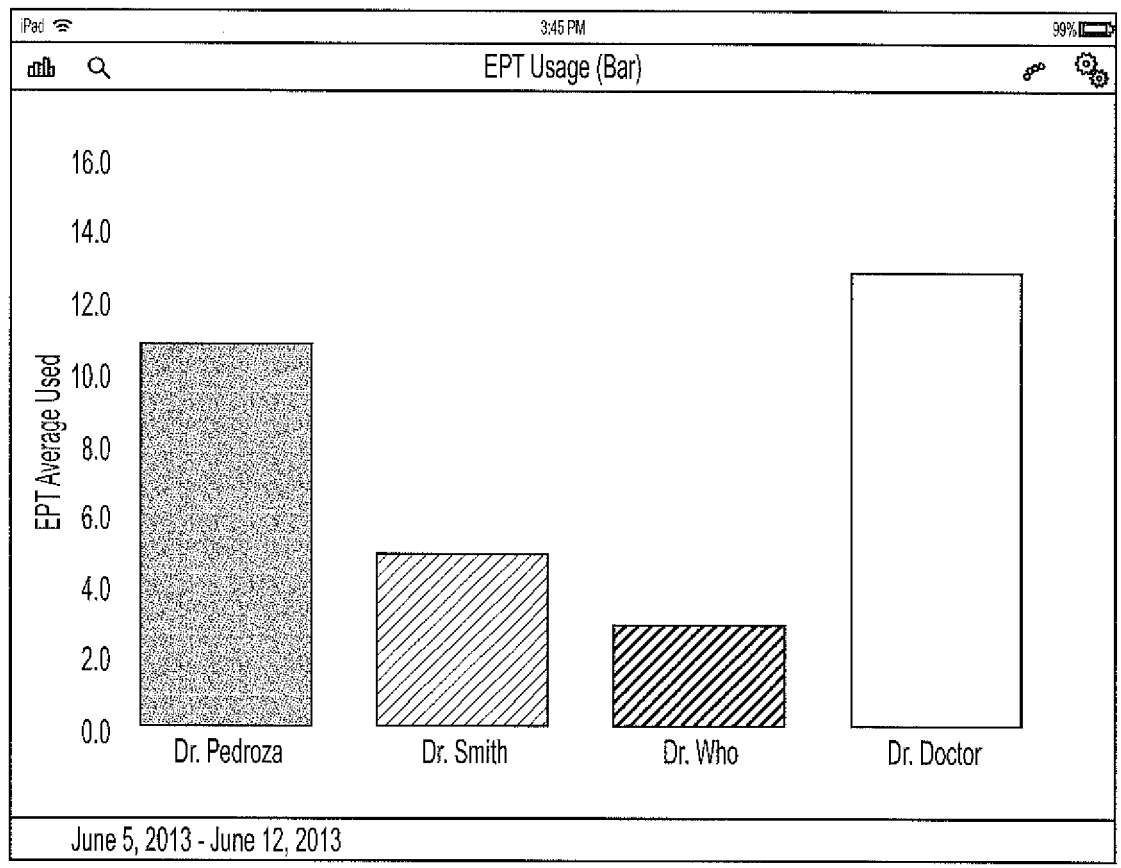

FIG. 10 shows a bar chart comparing average EPT by surgeon. The chart shows surgeon usage, and identifies total EPT usage by surgeon. EPT is averaged based on the actual number of cases performed.

Figure 11:
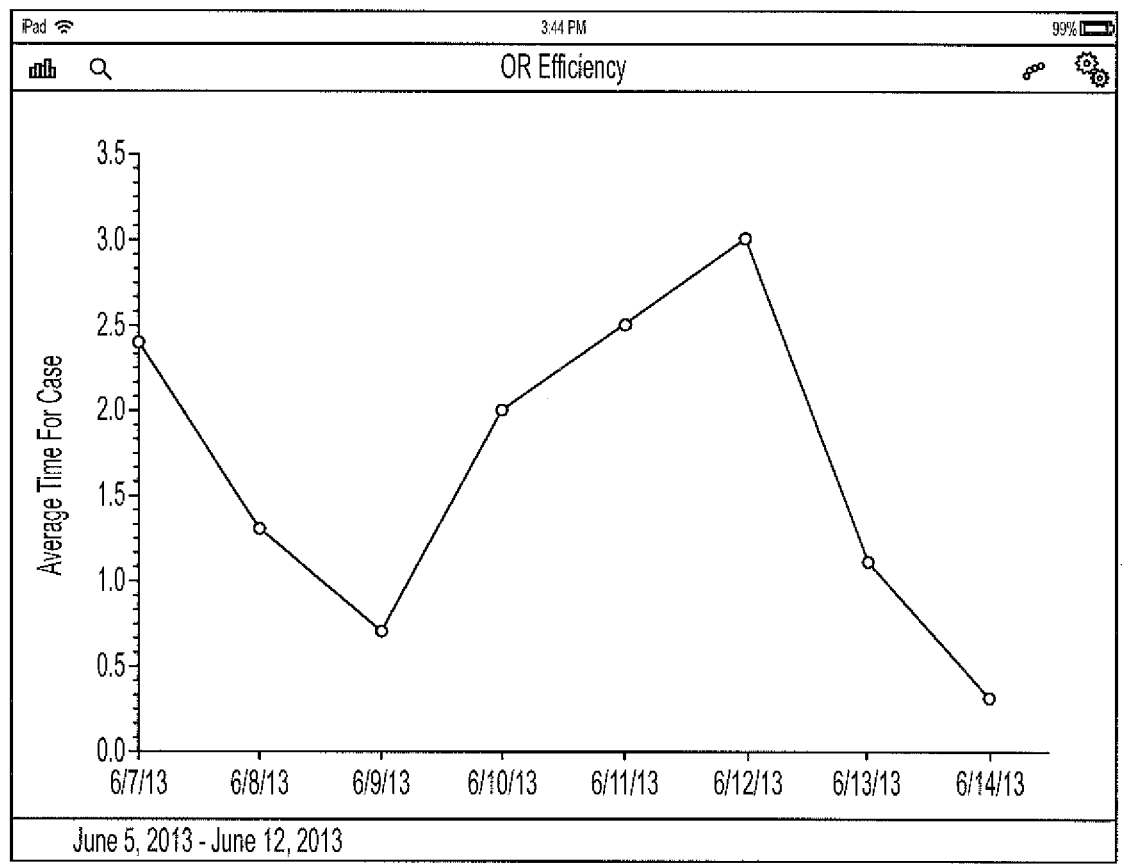

FIG. 11 shows a graph showing operating room trending. The line indicates operating room efficiency. Such a graph can identify, for example, how quickly the operating room is prepared for the next patient, and can provide trending information in a format that is understandable at a glance.

Figure 12:
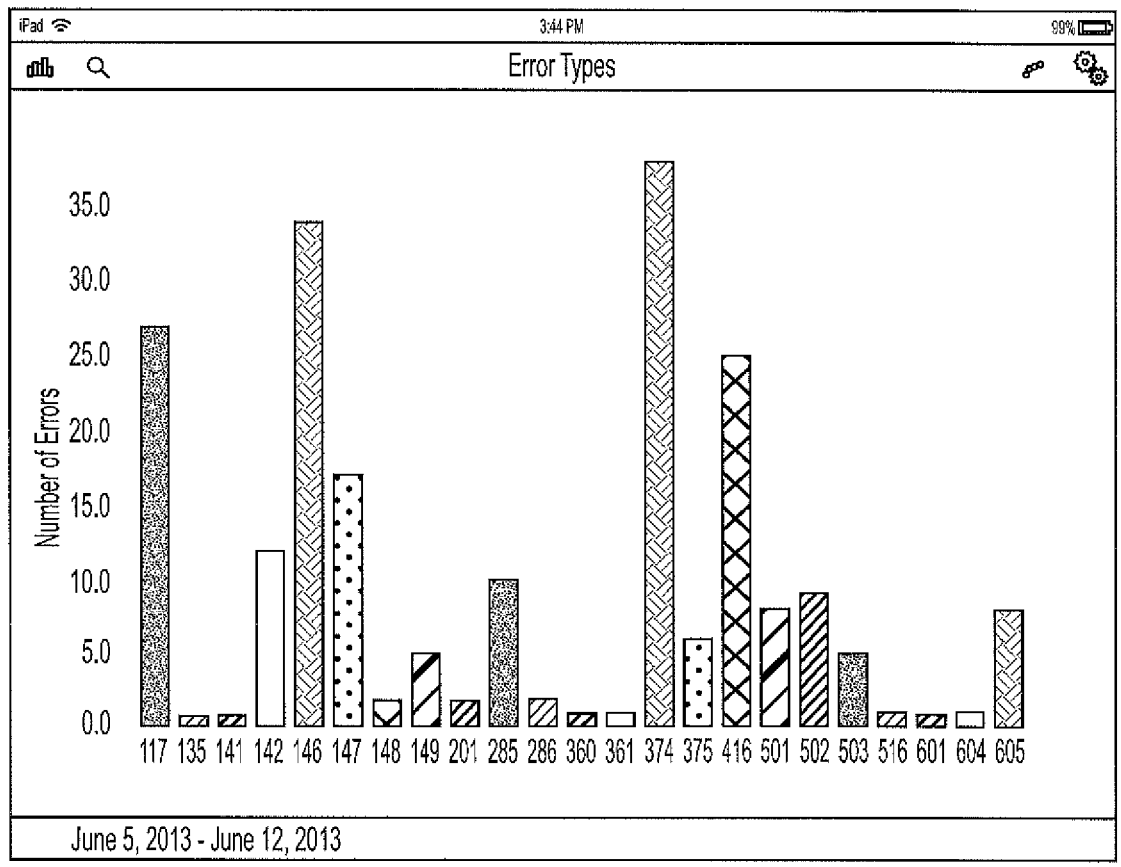

FIG. 12 is a bar chart showing system reliability. The chart shows system events, and can identify error and warning type messages, track user notifications, etc. Such a chart can be used to educate customers, provide preventative maintenance, trending information, and the like.

Although the invention has been described and illustrated in exemplary forms with a certain degree of particularity, it is noted that the description and illustrations have been made by way of example only. Numerous changes in the details of construction, combination, and arrangement of parts and steps may be made. Accordingly, such changes are intended to be included within the scope of the disclosure, the protected scope of which is defined by the claims.

What is claimed is:

1. A computer-based surgery support system, comprising:
a network attached computer with a processor and a data storage device storing instructions which, when executed on the processor, cause the computer to perform tasks including:
selecting one or more groups of settings for at least one surgical device used for a surgical procedure in an operating room;
receiving-information from the at least one surgical device;
correlating the information from the at least one surgical device and the one or more groups of settings;
storing the correlated information as stored information on the storage device in a database;
receiving a request for the stored information including an identified analysis of the information and an identified format of analysis results;
analyzing the stored information and formatting the analysis results in accordance with the received request;
providing the formatted analyzed information to a destination identified in the received request;
sending specific items of the stored information requested by a remote user to a user terminal remote from the at least one surgical device, wherein the specific items include the one or more groups of settings;
receiving at least one of a second one or more groups of settings configured by the remote user to control the at least one surgical device during a second surgical procedure from the user terminal remote from the at least one surgical device, the at least one of a second one or more groups of settings is based on the at least one of the one or more groups of settings;
automatically adjusting operating parameters of, and controlling operation of, the at least one surgical device based on the at least one of the second one or more groups of settings during the second surgical procedure; and
comparing and updating the information from the at least one surgical device and the second one or more groups of settings.

2. The system of claim 1, wherein the surgical procedure is an eye surgery.

3. The system of claim 2, wherein the eye surgery is one of cataract surgery, refractive surgery, laser cataract surgery, vitreoretinal surgery, and glaucoma surgery.

4. The system of claim 1, wherein at least a portion of the information from the at least one surgical device in use during the surgical procedure in the operating room is computer-readable information.

5. The system of claim 4, wherein the at least one surgical device is at least a part of network attached equipment in the operating room, and at least a portion of the computer-readable information is obtained from the network attached equipment in the operating room.

6. The system of claim 5, wherein the at least one surgical device includes a computer-based phacoemulsification system.

7. The system of claim 6, wherein the phacoemulsification system is configured to run at least one application utilizing selected settings during the procedure.

8. The system of claim 6, wherein the information from the at least one surgical device includes diagnostic information of the phacoemulsification system.

9. The system of claim 6, wherein the information from the at least one surgical device includes operational information of the phacoemulsification system recorded during the procedure.

10. The system of claim 9, wherein the operational information of the phacoemulsification system includes information sampled at regular intervals during the procedure.

11. The system of claim 9, wherein the operational information of the phacoemulsification system includes information recorded continuously during the procedure.

12. The system of claim 5, wherein the at least one surgical device includes a surgical media center (SMC) arranged to make at least one of an audio recording and a video recording of activity in the operating room during the surgical procedure.

13. The system of claim 12, wherein the tasks further include overlaying surgeon-dictated audio onto SMC data.

14. The system of claim 1, wherein the information from the at least one surgical device includes date and time of the beginning and end of the surgical procedure.

15. The system of claim 1, wherein the surgical procedure includes a plurality of stages, and the information from the at least one surgical device includes the date and time of the beginning and end of each of the stages.

16. The system of claim 1, wherein the tasks further include obtaining and storing identifiers of persons present during the procedure, including at least one of a patient on whom the procedure is performed, a surgeon performing the procedure, and operating room staff participating in the procedure and an indicator of their respective duties.

17. The system of claim 1, wherein the tasks further include obtaining and storing information of supplies consumed during the procedure, including an identity of the supplies and a respective amount used.

18. The system of claim 17 further comprising an interface to a supplier ordering system, wherein the tasks further include using the interface to order operating room supplies to replenish those consumed during the procedure.

19. The system of claim 18, wherein the using the interface to order the operating supplies further comprises using the interface to automatically order replenishing supplies after each procedure, according to a set schedule, or as triggered by inventory levels dropping to a predetermined threshold.

20. The system of claim 1, wherein the tasks further include gathering patient feedback information.

21. The system of claim 1, wherein the tasks further include providing feedback to a manufacturer of at least one device in the operating room.

22. The system of claim 21, wherein the feedback is provided to at least one of the manufacturer's customer service, marketing, sales, technical support, and research and development.

23. The system of claim 1, wherein the tasks further include generating at least one of a table, a graph, and text and providing the generated at least one of the table, the graph, and the text to the user terminal in response to the request.

24. The system of claim 1, wherein the plurality of procedures occur in a plurality of operating rooms.

25. The system of claim 1, wherein the formatted information includes at least one of operating room efficiency, effective phaco time (EPT), energy usage over time, energy usage flow rate, flow rate over time, vacuum rate, vacuum rate over time, procedure time, time between procedures, procedures per selected time period, characteristics of a plurality of surgeons, characteristics of a plurality of operating room staff persons, error logs of system or user errors, and a comparison of supplies used in a plurality of procedures.

26. The system of claim 1, wherein the analysis results include a correlation of information pertaining to a plurality of surgical procedures, efficiency, product usage, and phacoemulsification system program settings.

27. The system of claim 1, wherein the tasks further include receiving a type identifier of the user terminal, and formatting the specific items for presentation based on the identified user terminal type.

28. The system of claim 27, wherein the user terminal is one of a smart phone, a tablet computer, a portable computer, and a desktop computer.

29. The system of claim 1, wherein the information from the at least one surgical device includes at least one of an amount of energy applied to emulsify a lens, an amount of vacuum applied to aspirate, a flow rate, a microscopic view of an operating field, user selected settings of a phacoemulsification system used during the surgical procedure, diagnostic information of the phacoemulsification system, and operation information of the phacoemulsification system.

30. The system of claim 1, further comprising:
calculating an evaluation score for the surgical procedure based on the information from the at least one surgical device.

31. The system of claim 1, wherein the operations of the at least one surgical device that are controlled are selected from the group comprising vacuum rate, flow rate, aspiration rate, ultrasound power, bottle height, pressurized infusion rate, cut rate, diathermy power, and navigational control.

32. A computer-based cataract surgery support method, comprising:
selecting one or more groups of settings for at least one surgical device used for a surgical procedure in an operating room;
receiving information from the at least one surgical device;
correlating the information from the at least one surgical device and the one or more groups of settings;
storing the correlated information as stored information in a database;
receiving a request for the stored information including an identified analysis of the information and an identified format of analysis results;
analyzing the stored information;
formatting the analysis results in accordance with the received request;
providing the formatted analyzed information to a destination identified in the received request;
sending specific items of the stored information requested by a remote user to a user terminal remote from the at least one surgical device, wherein the specific items include the one or more groups of settings;
receiving at least one of a second one or more groups of settings configured by the remote user to control the at least one surgical device during a second surgical procedure from the user terminal remote from the at least one surgical device, the at least one of a second one or more groups of settings is based on the at least one of the one or more groups of settings;
automatically adjusting operating parameters of, and controlling operation of, the at least one surgical device based on the at least one of the second one or more groups of settings during the second surgical procedure; and
comparing and updating the information from the at least one surgical device and the second one or more groups of settings.

33. The method of claim 32, further comprising:
obtaining computer-readable information from a surgical media center (SMC) including at least one of an audio recording and a video recording of activity in the operating room during the surgical procedure.

34. The method of claim 33, further comprising:
overlaying surgeon-dictated audio onto SMC data to form overlaid data; and
storing the overlaid data in the database.

35. The method of claim 32, wherein the surgical procedure includes a plurality of stages, and the information from the at least one surgical device includes date and time of the beginning and end of each of the stages of the procedure and of the beginning and end of the surgical procedure.

36. The method of claim 32, further comprising obtaining identifiers of persons present during the procedure, including a patient on whom the procedure is performed, a surgeon performing the procedure, and operating room staff participating in the procedure and an indicator of their respective duties.

37. The method of claim 32, further comprising obtaining information of supplies consumed during the procedure, including an identity of the supplies and a respective amount used.

38. The method of claim 37, further comprising automatically ordering operating room supplies to replenish those consumed during the procedure after each procedure, according to a set schedule, or as triggered by inventory levels dropping to a predetermined threshold.

39. The method of claim 32, wherein the formatted information includes at least one of operating room efficiency, effective phaco time (EPT), energy usage over time, energy usage flow rate, flow rate over time, vacuum rate, vacuum rate over time, procedure time, time between procedures, procedures per selected time period, characteristics of a plurality of surgeons, characteristics of a plurality of operating room staff persons, error logs of system or user errors, and a comparison of supplies used in a plurality of procedures.

40. The method of claim 32, wherein the continuously correlating of the information is based on a plurality of surgical procedures, efficiency, product usage, and phacoemulsification system program settings.

41. The method of claim 32, further comprising: formatting the specific items for presentation based on an identified user terminal type of a remote terminal.

42. The method of claim 41, wherein the remote terminal is one of a smart phone, a tablet computer, a portable computer, and a desktop computer.

43. The method of claim 32, wherein the information from the at least one surgical device includes at least one of an amount of energy applied to emulsify a lens, an amount of vacuum applied to aspirate, a flow rate, a microscopic view of an operating field, user selected settings of a phacoemulsification system used during the surgical procedure, diagnostic information of the phacoemulsification system, and operation information of the phacoemulsification system.

44. The method of claim 32, further comprising:
calculating an evaluation score for the surgical procedure based on the information from the at least one surgical device.

45. The method of claim 32, wherein the operations of the at least one surgical device that are controlled are selected from the group comprising vacuum rate, flow rate, aspiration rate, ultrasound power, bottle height, pressurized infusion rate, cut rate, diathermy power, and navigational control.

* * * * *